United States Patent
Bordier et al.

(10) Patent No.: US 11,512,050 B2
(45) Date of Patent: Nov. 29, 2022

(54) PROCESS FOR PERHYDROLYSIS OF ALIPHATIC EPOXIDES

(71) Applicants: DEMETA, Rennes (FR); UNIVERSITE DE RENNES 1, Rennes (FR)

(72) Inventors: Corentin Bordier, Saint-Calais (FR); Vincent Escande, Rennes (FR); Frédéric Caijo, Thorigne Fouillard (FR); Christophe Darcel, Rennes (FR)

(73) Assignees: DEMETA, Rennes (FR); UNIVERSITE DE RENNES 1, Rennes (FR)

( * ) Notice: Subject to any disclaimer, the term of this patent is extended or adjusted under 35 U.S.C. 154(b) by 0 days.

(21) Appl. No.: 17/432,504

(22) PCT Filed: Feb. 20, 2020

(86) PCT No.: PCT/FR2020/050320
§ 371 (c)(1),
(2) Date: Aug. 20, 2021

(87) PCT Pub. No.: WO2020/169932
PCT Pub. Date: Aug. 27, 2020

(65) Prior Publication Data
US 2022/0169601 A1  Jun. 2, 2022

(30) Foreign Application Priority Data
Feb. 21, 2019 (FR) .................................. 1901723

(51) Int. Cl.
*C07C 407/00* (2006.01)

(52) U.S. Cl.
CPC .................................. *C07C 407/00* (2013.01)

(58) Field of Classification Search
CPC .................................................... C07C 407/00
See application file for complete search history.

(56) References Cited

FOREIGN PATENT DOCUMENTS

JP    2003-342255    12/2003

OTHER PUBLICATIONS

Miaomiao, L. et al. "Preparation of Nonanal by Oxidation Cleavage of Methyl Erucate" *Chemical Industry Times*, Apr. 4, 2012, pp. 19-22, vol. 26, No. 4.
Translation of Chinese Office Action in Application No. 202080014927.4, dated Dec. 10, 2021, pp. 1-6.
Li, Y. et al. "Facile Ring-Opening of Oxiranes by $H_2O_2$ Catalyzed by Phosphomolybdic Acid" *Organic Letters*, 2009, pp. 2691-2694, supporting information pp. S1-S33, vol. 11, No. 12.
Written Opinion in International Application No. PCT/FR2020/050320, dated Jun. 3, 2020, pp. 1-7.

*Primary Examiner* — Sikarl A Witherspoon
(74) *Attorney, Agent, or Firm* — Saliwanchik, Lloyd & Eisenschenk

(57) ABSTRACT

The present invention relates to a process for synthesizing hydroperoxy alcohols by perhydrolysis of epoxides, using an aqueous solution of hydrogen peroxide, in the presence of a catalyst consisting of phosphotungstic acid.

11 Claims, No Drawings

PROCESS FOR PERHYDROLYSIS OF ALIPHATIC EPOXIDES

CROSS-REFERENCE TO RELATED APPLICATION

This application is the U.S. national stage application of International Patent Application No. PCT/FR2020/050320, filed Feb. 20, 2020.

SUBJECT MATTER OF THE INVENTION

The present invention relates to a process for synthesizing hydroperoxy alcohols by perhydrolysis of epoxides, using an aqueous solution of hydrogen peroxide, in the presence of a catalyst consisting of phosphotungstic acid.

BACKGROUND OF THE INVENTION

The β-hydroperoxy alcohol (HPA) unit is a functional group that is particularly useful in organic synthesis. It constitutes a precursor allowing the formation of aldehydes, protective groups of carbonyl functions, or of 1,2,4-trioxanes, the unit responsible for the pharmacological activity of a great many molecules for antimalarial use.[1]

The synthesis of the HPA unit has been described by epoxide perhydrolysis, said epoxide being either isolated, or formed in situ by epoxidation of an alkene. Epoxide perhydrolysis consists of having hydrogen peroxide (either in aqueous solution, or anhydrous) act as a nucleophilic reagent on an epoxide, the electrophilic character of which is accentuated by activation by means of an acid catalyst.

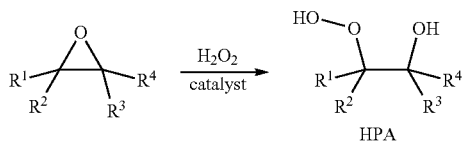

HPA

Various Brønsted or Lewis acid catalysts have been described for this reaction: tungstic acid and derivatives thereof,[2,3] molybdenum(VI) salts,[4,5] perchloric acid,[6] trifluoroacetic acid,[7] tetrakis(oxodiperoxotungsto)phosphate,[8] antimony(III) salts,[9] or phosphomolybdic acid.[1]

Although these methods lead to formation of the HPA unit, they suffer from several technical limitations, which are problematic with a view to application on an industrial scale.

In fact, since the production of HPA competes with formation of the corresponding diol, most of the methods make use of hydrogen peroxide at a very high concentration (>90% w/v), or even anhydrous,[2,4,6,10] or even anhydrous ethereal extracts of peroxide hydrogen,[1,5,9] in order to discourage formation of the diol. In these conditions, there are considerable risks of explosion, which are reported by the authors of these methods.[1,2,9]

An alternative is to use hydrogen peroxide at lower concentration, but in this case high levels of catalyst are necessary to promote the formation of HPA at the expense of the diol.

Catalyst charges of the order of 10 wt % are for example used conventionally in the case of the substrate oleic acid.[3,8] Thus, patent application JP 2003/342255 describes a process for oxidation of oleic acid to the corresponding hydroperoxy alcohol. The reaction is carried out in the presence of from 1 to 20 wt %, for example 10 wt %, of a catalyst such as $H_2WO_4$, $H_2MoO_4$, $MoO_3$, or $H_3PMo_{12}O_{40}$, and two equivalents of $H_2O_2$ at 30-60%, at 35° C. and in a solvent that dissolves both the substrate and the catalyst, such as tert-butanol. However, mixtures of the hydroperoxy alcohol and of the corresponding 1,2-diol are formed, and moderate yields of hydroperoxy alcohol between 4 and 50% are obtained, after relatively long reaction times, of the order of at least five hours, or even fifteen hours, to reach a degree of conversion of at least 75%. The low activity of the catalysts used is reflected moreover in a very low turnover number or TON (corresponding to the ratio of the molar amount of hydroperoxy alcohol produced to the molar amount of catalyst), for example of 4 in the case of tungstic acid.

These various technical problems hold back the industrial preparation of compounds incorporating the HPA unit by epoxide perhydrolysis.

In this context, there is still a need to develop a process for perhydrolysis of epoxides that can meet the industrial requirements, both in terms of safety and economic criteria.

More precisely, it is desirable to propose a method of synthesis leading to high yields of HPA (above 60%) in less than four hours, and/or at high turnover numbers (above 300), and without using hydrogen peroxide at a concentration that is dangerous to handle (maximum 70% w/v).

The inventors have demonstrated that this result could be achieved by carrying out the perhydrolysis reaction on an epoxidized substrate in the presence of a particular catalyst, phosphotungstic acid $H_3PW_{12}O_{40}$, used in a maximum amount that is five times, or even ten times, lower than the lowest value recommended in document JP 2003/342255. This process can be applied in simple, mild conditions, not necessarily requiring heating or the use of an organic solvent, which constitutes additional advantages of this process from the economic and environmental standpoint.

SUMMARY OF THE INVENTION

The invention relates to a process for synthesizing hydroperoxy alcohols of formula (Ia) and/or (Ib):

where:

$R^1$ and $R^2$ represent, each independently, an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NW, and R and R' denote, each independently, a group selected from: a hydrogen atom, a $C_1$-$C_6$ alkyl group or a group —(CH$_2$)—CH(OCOR$^5$)—CHOCOR$^6$, R$^5$ and R$^6$ denoting, each independently, a linear or branched $C_8$-$C_{22}$ alkyl group optionally substituted and/or interrupted by at least one hydroperoxy and/or hydroxy group, or else W and R$^2$ together form a carbocycle consisting of 6 to 12 ring members and optionally substituted, $R^3$ and $R^4$ represent, each independently, a hydrogen atom or an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NW, and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one hydroperoxy and/or hydroxy group, characterized in that it comprises a step of perhydrolysis of the epoxide of formula (II):

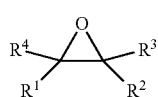

(II)

where:

W and $R^2$ represent, each independently, an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NW, and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one epoxy group, or else $R^1$ and $R^2$ together form a carbocycle consisting of 6 to 12 ring members and optionally substituted, $R^3$ and $R^4$ represent, each independently, a hydrogen atom or an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NW, and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one epoxy group, by reaction with an aqueous solution of hydrogen peroxide, in the presence of a catalyst consisting of phosphotungstic acid, said catalyst representing from 10 to 2000 ppm molar, relative to the number of moles of epoxide of formula (II).

DETAILED DESCRIPTION

Definitions

"Alkyl" means a saturated, linear or branched acyclic hydrocarbon group. Examples of alkyl having 1 to 6 carbon atoms (or "$C_1$-$C_6$") are in particular, a methyl, an ethyl, a propyl, an isopropyl, a butyl, a tert-butyl, a pentyl, or a hexyl.

"Alkylene" means a saturated, linear or branched divalent acyclic hydrocarbon group. Examples of alkylene having 1 to 12 carbon atoms are in particular, a methylene, an ethylene, a propylene, a butylene, a pentylene, a hexylene, a heptylene, an octylene, a nonylene, a decylene, an undecylene, or a dodecylene.

"Carbocycle" means an optionally unsaturated, aliphatic or aromatic, preferably aliphatic, mono- or polycyclic hydrocarbon group. Examples of carbocycle having 6 to 12 ring members are in particular, a cyclohexyl, a cycloheptyl, a cyclooctyl, or a cyclododecyl.

"Alkoxy" or "alkyloxy" means an alkyl as defined above, attached to the rest of the molecule via an —O— bond ("—O-alkyl"). An example of alkoxy is in particular a methoxy group.

"Acyloxy" means a group of formula —O—C(O)—R" where R" is a saturated or unsaturated, linear or branched, cyclic or acyclic, aromatic or aliphatic hydrocarbon group. An example of acyloxy group is an acetoxy group (—O—C(O)—$CH_3$).

This invention relates to a process for synthesizing hydroperoxy alcohols, denoted hereinafter by "HPA", following a reaction of perhydrolysis of epoxides.

The epoxides usable in the present invention have the formula:

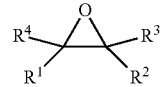

In a first embodiment of the invention, $R^1$ and $R^2$ represent, each independently, an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NR', and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one epoxide group —CH(O)CH—.

The alkylene chain L and the alkyl groups of R', $R^3$ and $R^4$ may, independently of one another, be substituted with at least one group selected from: a hydroxyl group, an acyloxy group containing from 2 to 8 carbon atoms and an alkoxy group containing from 1 to 6 carbon atoms. Preferred substituents are the methoxy, hydroxyl and acetoxy groups.

Preferably, X denotes an oxygen atom. Furthermore, preferably $R^3$=$R^4$=H.

When $R^2$ denotes a group -L-A where A is a hydrogen atom, preferably L denotes an alkylene chain containing from 4 to 12, more preferably from 4 to 8 carbon atoms and $R^1$ represents a $C_4$-$C_{12}$ alkyl group. An example of epoxide corresponding to this definition is the oxide of tetradec-7-ene. As a variant, L may represent a bond. An example of such an epoxide is the oxide of octadec-1-ene. In a particular embodiment, $R^1$ or $R^2$ is -L-A where A is a hydrogen atom and L is a bond.

When $R^2$ denotes a group -L-A where A denotes a group —COXR, preferably L denotes an alkylene chain containing from 5 to 12, more preferably from 7 to 11 carbon atoms and $R^1$ represents a $C_6$-$C_{10}$ alkyl group. Preferably, X=O. The group R then represents advantageously a hydrogen atom or a methyl group. Examples of epoxides corresponding to this definition are the methyl ester of epoxidized erucic acid (or 13,14-epoxy-methyl docosanoate) and epoxidized oleic acid (or 9,10-epoxy-methyl octadecanoate).

As a variant, group A may represent a group —($CH_2$)—CH(OCOR$^5$)—CHOCOR$^6$, where $R^5$ and $R^6$ denote, each independently, a $C_8$-$C_{22}$ alkyl group optionally interrupted by at least one epoxide group —CH(O)CH—. The epoxide used according to the invention then corresponds to a triglyceride of one or more fatty acids, which may be identical or different, preferably identical. An example of such a compound is the triglyceride of epoxidized oleic acid (or glyceryl tri(9,10-epoxyoctadecanoate)).

According to yet another possibility, $R^2$ denotes a group -L-A where L is a bond and A denotes a group —COXR. X is preferably an oxygen atom. The group R then represents advantageously a hydrogen atom or a $C_1$-$C_6$ alkyl group. Examples of epoxides corresponding to this definition are epoxymaleic acid, epoxyfumaric acid and esters thereof.

In a second embodiment of the invention, $R^1$ and $R^2$ together form a carbocycle consisting of 6 to 12 ring members that is optionally substituted with at least one linear or branched $C_1$-$C_6$ alkyl group. Examples of epoxides corresponding to this definition are given below:

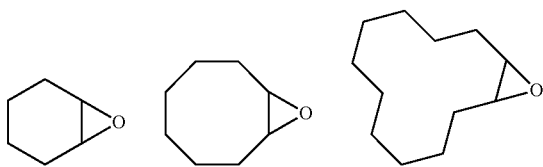

In a particular embodiment of the invention, the epoxide of formula (II) is the product of epoxidation of a terpene. The terpenes comprise in particular the monoterpenes, sesquiterpenes, diterpenes, sesterpenes, triterpenes, carotenoids or terpenoids. Examples of terpenes are in particular α-pinene, β-pinene, carene, limonene, a carotene, ocimene, myrcene, citronellene, methoxycitronellene, farnesene, squalene, astaxanthin, or 7-methoxy-3,7-dimethyloct-1-ene, this list not being exhaustive.

In a preferred embodiment of the invention, the epoxide of formula (II) is the product of epoxidation of a mono- or polyunsaturated fatty acid or of an ester thereof, in particular an alkyl ester or a glyceride of said fatty acid. The compound of formula (II) may thus be selected from the products of epoxidation of palmitoleic acid, oleic acid, erucic acid or nervonic acid, or an ester thereof, preferably the compound of formula (II) is the product of epoxidation of oleic acid or of an ester thereof. The fatty acid or its glyceride may itself be derived from a vegetable oil. For its part, the fatty acid alkyl ester may be obtained by transesterification of at least one vegetable oil.

As examples of vegetable oils, we may mention in particular wheat germ oil, sunflower oil, argan oil, hibiscus oil, coriander oil, grapeseed oil, sesame oil, maize oil, apricot oil, castor oil, karite oil, avocado oil, olive oil, soybean oil, sweet almond oil, palm oil, colza oil, cotton oil, hazelnut oil, macadamia oil, jojoba oil, alfalfa oil, poppy oil, Chinese okra oil, sesame oil, cucurbit oil, blackcurrant oil, evening primrose oil, lavender oil, borage oil, millet oil, barley oil, quinoa oil, rye oil, safflower oil, candlenut oil, passionflower oil, musk rose oil, Echium oil, wild flax oil or camellia oil.

The epoxidation of the vegetable oils may be carried out in a conventional manner known by a person skilled in the art, and similarly for their optional transesterification. It is generally preferred to carry out transesterification before epoxidation.

In another embodiment, the substrate used in the perhydrolysis reaction is the product of epoxidation of an alkene. Once again, epoxidation may be carried out in a conventional manner known by a person skilled in the art, for example by means of a carboxylic peracid.

Regardless of what substrate of the epoxide type is used, the process according to the invention consists of transforming the epoxide into HPA by perhydrolysis, by adding a solution of hydrogen peroxide to the epoxide, in the presence of a particular catalyst that consists of phosphotungstic acid.

The solution of hydrogen peroxide is at a concentration of at least 30%, or even at least 45%, and at most 60%, or even 70%, for example at 30%, 45%, 60% or 70% (w/v). It was observed that a higher concentration of hydrogen peroxide led to a quicker reaction, being reflected in a degree of conversion of at least 90%, preferably more than 95%, or even more than 99%, in less than four hours. The hydrogen peroxide is usually used in an amount from 1 to 1.5 molar equivalent, preferably at a rate of 1.1 to 1.3 molar equivalent, relative to the epoxide.

For its part, the catalyst is generally used in an amount from 0.01 to 2 wt %, for example at least 0.1 wt % or at least 0.2 wt %, in particular at least 0.4 wt % or at least 0.5 wt %, and for example at most 1.5 wt %, in particular at most 1 wt %, relative to the weight of epoxide. The amount of catalyst used represents moreover at least 10 ppm molar, for example at least 50 ppm molar or even at least 100 ppm molar, in particular at least 200 ppm molar, or even at least 400 ppm molar or even at least 800 ppm molar and at most 2000 ppm molar, advantageously at most 1500 ppm molar, or even at most 1000 ppm molar, relative to the molar amount of epoxide.

The perhydrolysis reaction may be carried out at a temperature from 5 to 60° C., preferably from 20 to 60° C., and more preferably from 30 to 50° C., for a time from 10 minutes to 4 hours, preferably from 45 minutes to 2.5 h. It was observed that the catalyst used according to the invention in fact made it possible to reach a degree of conversion of the epoxide of at least 90%, preferably at least 95%, or even at least 99%, after the stated interval of time (as measured by $^1$H NMR). The duration of the reaction is shorter the higher the temperature, within the aforementioned ranges.

The aforementioned reactants (epoxide, hydrogen peroxide and catalyst) may be introduced in any order into the reactor in which the reaction is carried out. It is preferred, moreover, for the perhydrolysis reaction to be carried out in the absence of organic solvent, i.e. a compound capable of dissolving the epoxide and/or the catalyst and whose structure contains one or more carbon atoms. Examples of such solvents are in particular the polar protic solvents such as alcohols. It has in fact been demonstrated that these solvents slowed down the perhydrolysis reaction at room temperature and generally lowered the yield of HPA.

The process described above generally makes it possible to obtain the required HPA with a yield of at least 60%, preferably at least 65%, or else at least 70%, generally at least 80%, or even at least 85% or even at least 90%. Moreover, the turnover number (TON) of the reaction is always above 300, generally above 700 and may be up to 15 000, or even up to 20 000 or even 50 000. Generally a mixture of HPA of formulas (Ia) and (Ib) is obtained.

This process may be used in the oxidative cleavage of epoxidized vegetable oils, in particular for forming fatty aldehydes and/or fatty acids. Transformation of the HPA obtained according to the invention into aldehydes and/or acids may be carried out in a conventional manner known by a person skilled in the art, by acid or basic catalysis or by a radical route.

EXAMPLES

The invention will be better understood from the following examples, which are given purely for purposes of illustration and do not have the aim of limiting the scope of the invention, which is defined by the accompanying claims.

Materials and Methods

The reactants were obtained from usual commercial suppliers (Sigma-Aldrich-Merck, Acros, Alfa-Aesar, Fisher) and were used without prior purification. Thermogravimetric analysis reveals that the commercial hydrated phosphotungstic acid contains 7.87% (w/w) of water. The amounts of substance indicated hereunder therefore correspond to the commercial hydrated phosphotungstic acid. Methyl 9,10-epoxystearate is prepared according to a procedure in the literature[11] and is obtained with a purity from 82 to 99%.

NMR analysis: the nuclear magnetic resonance (NMR) spectra of the proton were recorded on an AVANCE 400 NMR spectrometer at 400.1 MHz (Bruker) at 25° C. The chemical shifts are expressed in ppm (parts per million) relative to the signal of the residual nondeuterated solvent. The multiplicity of the signals is described as follows: singlet (s), doublet (d), triplet (t) and multiplet (m).

TGA analysis: The thermogravimetric analyses were carried out using TGA-DSC-1 Mettler-Toledo apparatus under an anhydrous dinitrogen stream with a heating rate of 10° C./min.

Example 1: Perhydrolysis of Methyl 9,10-Epoxystearate—Effect of Temperature

A 6-mL test tube (ø12.25×75×0.80 mm) equipped with a magnetic bar is charged with 0.506 mmol of methyl 9,10-epoxystearate, 0.48 μmol of hydrated phosphotungstic acid and 0.617 mmol (35 μL) of aqueous solution of hydrogen peroxide at 60% w/v. The mixture is stirred at a given temperature for a given time, indicated in the following table. At the end of the time with stirring, $^1$H NMR analysis of the crude reaction product diluted in 0.5 mL of deuterated chloroform ($CDCl_3$) shows that the methyl 9,10-epoxystearate is converted completely into a mixture of methyl 9(10)-hydroperoxy-10(9)-hydroxystearate (HPA) and methyl 9,10-dihydroxystearate in the proportions given in the following table:

TABLE 1

| Temp.[a] (° C.) | Time (min) | Catalyst charge (wt %) | Catalyst charge (mol ppm) | TON | Conv. (%)[a] | Yld. HPA (%)[a] | Yld. diol (%)[a] | Mass balance (%) |
|---|---|---|---|---|---|---|---|---|
| 30 | 60 | 0.968 | 968 | 770 | >99 | 74 | 12 | 87 |
| 50 | 10 | 0.914 | 913 | 830 | >99 | 76 | 13 | 89 |

[a]Degree of conversion (Conv.) and yield (Yld.) determined by $^1$H NMR of the crude reaction product diluted in $CDCl_3$.

As this test shows, an increase in temperature makes it possible to obtain a TON that is a little higher in a shorter time, but does not have a significant effect on the degree of conversion and the selectivity for HPA, so that the reaction can be carried out at a temperature close to room temperature.

Example 2: Perhydrolysis of Methyl 9,10-Epoxystearate—Effect of the Concentration of the Aqueous Solution of Hydrogen Peroxide A 6-mL test tube (ø12.25×75×0.80 mm) equipped with a magnetic bar is charged with 0.506 mmol of methyl 9,10-epoxystearate, 0.48 μmol of hydrated phosphotungstic acid and the aqueous solution of hydrogen peroxide of known concentration (0.617 mmol). The mixture is stirred at 30° C. for a period of one hour. At the end of stirring, $^1$H NMR analysis of the crude reaction product diluted in 0.5 mL of deuterated chloroform ($CDCl_3$) shows that the methyl 9,10-epoxystearate is converted into a mixture of methyl 9(10)-hydroperoxy-10(9)-hydroxystearate (HPA) and methyl 9,10-dihydroxystearate in the proportions given in the following table:

TABLE 2

| Concentration $H_2O_2$ (% w/v) | Catalyst charge (wt %) | Catalyst charge (mol ppm) | TON | Conv. (%)[a] | Yld. HPA (%)[a] | Yld. diol (%)[a] | Mass balance (%) |
|---|---|---|---|---|---|---|---|
| 3 | 0.975 | 975 | 140 | 18 | 13 | 4 | 99 |
| 30 | 0.922 | 922 | 740 | 82 | 68 | 10 | 96 |
| 30[b] | 0.806 | 806 | 910 | >99 | 73 | 9 | 82 |
| 30[c] | 0.922 | 922 | 890 | >99 | 82 | 12 | 94 |
| 60 | 0.968 | 968 | 770 | >99 | 74 | 12 | 87 |
| 70 | 1.040 | 1040 | 770 | >99 | 79 | 9 | 88 |

[a]Degree of conversion (Conv.) and yield (Yld.) determined by $^1$H NMR of the crude reaction product diluted $CDCl_3$
[b]2 h 10 min of reaction instead of one hour.
[c]16 h of reaction instead of one hour.

It is clear from this test that the use of a concentration of hydrogen peroxide above 30% (w/v) makes it possible to reach a degree of conversion greater than 99% in just one hour.

Example 3: Perhydrolysis of Methyl 9,10-Epoxystearate—Effect of the Catalyst Charge A 6-mL test tube (ø12.25×75×0.80 mm) equipped with a magnetic bar is charged with 1.050 mmol of methyl 9,10-epoxystearate, a known amount of hydrated phosphotungstic acid and 1.280 mmol (72.6 μL) of aqueous solution of hydrogen peroxide at 60% w/v. The mixture is stirred at 30° C. for a given length of time. At the end of stirring, $^1$H NMR analysis of the crude reaction product diluted in 0.5 mL of deuterated chloroform ($CDCl_3$) shows that the methyl 9,10-epoxystearate is converted into a mixture of methyl 9(10)-hydroperoxy-10(9)-hydroxystearate (HPA) and methyl 9,10-dihydroxystearate in the proportions given in the following table:

| Reaction time | Catalyst charge (wt %) | Catalyst charge (mol ppm) | TON | Conv. (%)[a] | Yld. HPA (%)[a] | Yld. diol (%)[a] | Mass balance (%) |
|---|---|---|---|---|---|---|---|
| 1 h | 0 | 0 | 0 | 0 | 0 | 0 | 100 |
| 1 h | 0.116 | 116 | 2200 | 29 | 26 | 3 | 100 |
| 29 h 15 min | 0.116 | 116 | 5400 | 71 | 63 | 8 | 100 |
| 1 h | 0.242 | 242 | 3300 | 91 | 79 | 10 | 98 |
| 2 h | 0.242 | 242 | 3400 | >99 | 83 | 11 | 94 |
| 1 h | 0.481 | 481 | 1700 | >99 | 84 | 11 | 95 |
| 1 h | 0.968 | 968 | 770 | >99 | 74 | 12 | 87 |
| 1 h | 10.8 | 10800 | 22 | >99 | 24 | 19 | 43 |

[a]Degree of conversion (Conv.) and yield (Yld.) determined by $^1$H NMR of the crude reaction product diluted in $CDCl_3$ It is clear from this table that at 30° C., a degree of conversion greater than 99% can be obtained with a catalyst charge below 1 wt % and that it can even be lowered to 0.2 wt % without substantially increasing the reaction time or affecting the yield of HPA. Furthermore, a catalyst charge of the order of 10 wt % does not allow the desired yield of HPA to be achieved and has an adverse effect on the TON of the reaction.

Example 4: Perhydrolysis of Methyl 9,10-Epoxystearate—Investigation of the Reaction at 50° C.

A 6-mL test tube (ø12.25×75×0.80 mm) equipped with a magnetic bar is charged with methyl 9,10-epoxystearate in a variable amount, 0.110 µmol of hydrated phosphotungstic acid and an aqueous solution of hydrogen peroxide at 60% w/v in a variable amount (1.2 molar eq.). The mixture is stirred at 50° C. for a given length of time. At the end of stirring, $^1$H NMR analysis of the crude reaction product diluted in 0.5 mL of deuterated chloroform (CDCl$_3$) shows that the methyl 9,10-epoxystearate is converted into a mixture of methyl 9(10)-hydroperoxy-10(9)-hydroxystearate (HPA) and methyl 9,10-dihydroxystearate in the proportions given in the following table:

TABLE 4

| Reaction time | Catalyst charge (wt %) | Catalyst charge (mol ppm) | TON | Conv. (%)[a] | Yld. HPA (%)[a] | Yld. diol (%)[a] | Mass balance (%)[a] |
|---|---|---|---|---|---|---|---|
| 15 min | 0.014 | 14 | 0 | 3 | 0 | 0 | 97 |
| 1 h 10 | 0.014 | 14 | 10700 | 16 | 15 | 1 | 100 |
| 2 h 20 | 0.014 | 14 | 11400 | 19 | 16 | 3 | 100 |
| 15 min | 0.028 | 28 | 7200 | 22 | 20 | 2 | 100 |
| 1 h 10 | 0.028 | 28 | 8800 | 27 | 25 | 2 | 100 |
| 2 h 20 | 0.028 | 28 | 6800 | 22 | 19 | 2 | 99 |
| 15 min | 0.055 | 55 | 13800 | 80 | 76 | 4 | 100 |
| 1 h 10 | 0.055 | 55 | 15600 | 90 | 86 | 4 | 100 |
| 15 min | 0.112 | 112 | 7800 | 97 | 88 | 7 | 98 |
| 1 h 10 | 0.112 | 112 | 8300 | >99 | 93 | 7 | 100 |

[a]Degree of conversion (Conv.) and yield (Yld.) determined by $^1$H NMR of the crude reaction product diluted in CDCl$_3$ It is clear from this table that at 50° C., a degree of conversion of at least 90% can be obtained with a catalyst charge below 1 wt % and that it can even be lowered to 0.05 wt % without any marked effect on the yield of HPA.

Example 5: Perhydrolysis of Methyl 9,10-Epoxystearate—Effect of Addition of Solvent A 6-mL test tube (ø12.25×75×0.80 mm) equipped with a magnetic bar is charged with 1.23 mmol of methyl 9,10-epoxystearate, 0.99 µmol of hydrated phosphotungstic acid, 1900 µL of t-BuOH and an aqueous solution of hydrogen peroxide at 30% (w/v) (1.25 mmol). The mixture is stirred at a certain temperature for a given length of time. At the end of stirring, $^1$H NMR analysis of the crude reaction product diluted in 0.5 mL of deuterated chloroform (CDCl$_3$) shows that the methyl 9,10-epoxystearate is converted into a mixture of methyl 9(10)-hydroperoxy-10(9)-hydroxystearate (HPA) and methyl 9,10-dihydroxystearate in the proportions given in the following table:

TABLE 5

| Time | Temp (° C.) | Catalyst charge (wt %) | Catalyst charge (mol ppm) | TON | Conv. (%)[a] | Yld. HPA (%)[a] | Yld. diol (%)[a] | Mass balance (%)[a] |
|---|---|---|---|---|---|---|---|---|
| 2 h 10 | 30 | 0.781 | 781 | 830 | 85 | 65 | 13 | 93 |
| 5 h | 30 | 0.781 | 781 | 1000 | >99 | 78 | 15 | 93 |
| 1 h 05 | 50 | 0.833 | 833 | 890 | 99 | 74 | 18 | 93 |

[a]Degree of conversion (Conv.) and yield (Yld.) determined by $^1$H NMR of the crude reaction product diluted in CDCl$_3$ As is clear from this table, the presence of an organic solvent in the reaction mixture does not always make it possible to achieve a maximum degree of conversion of the epoxide and an acceptable yield of HPA in about two hours at most. This problem can be overcome with slight heating of the reaction mixture.

In the absence of solvent, however, a maximum degree of conversion is obtained in at most 2 h 10 min with an acceptable yield, even at 30° C., as shown in Example 2. Furthermore, it was observed that at the highest concentrations of hydrogen peroxide, absence of solvent also makes it possible to achieve a marked increase in the yield of HPA. In fact, when the perhydrolysis reaction is carried out in the conditions of Example 1, but in the presence of 950 µL of tert-butanol, the yield of HPA is only 47% (instead of 74%) after one hour at 30° C. and 58% (instead of 76%) after 10 minutes at 50° C.

Example 6: Perhydrolysis of 2-(6-methoxy-6-methylheptan-2-yl)oxirane

A 6-mL test tube (012.25×75×0.80 mm) equipped with a magnetic bar is charged with 1.00 mmol of 2-(6-methoxy-6-methylheptan-2-yl)oxirane, 0.13 µmol of hydrated phosphotungstic acid and an aqueous solution of hydrogen peroxide at 60% (w/v) (1.01 mmol). The mixture is stirred at 1000 rev/min at 50° C. for 3 hours. At the end of stirring and at room temperature, 0.14 mmol of hexafluorobenzene is added to the reaction mixture, to serve as an internal standard for quantification of the reaction products. $^{13}$C NMR quantitative analysis of the crude reaction product diluted in 0.5 mL of deuterated dichloromethane (CD$_2$Cl$_2$) shows that the 2-(6-methoxy-6-methylheptan-2-yl)oxirane is converted into a mixture made up of 1(2)-hydroperoxy-7-methoxy-3,7-dimethyloctan-2(1)-ol (HPA) and 7-methoxy-3,7-dimethyloctane-1,2-diol, obtained with yields of 66 mol % and 34 mol %, respectively. A TON of 5000 is thus achieved.

Example 7: Perhydrolysis of 7-oxabicyclo[4.1.0]heptane

A 19-mL test tube (ø16×150×3.3 mm) equipped with a magnetic bar is charged with 5.93 mmol of 7-oxabicyclo [4.1.0]heptane, 0.70 µmol of hydrated phosphotungstic acid and 0.5 mL of deuterated dichloromethane. This test tube is then placed in a bath thermostatically controlled to 5° C. and then it is stirred slowly for 30 minutes. After this time, the stirring is set at 1000 rev/min and then an aqueous solution of hydrogen peroxide at 60% (w/v) (6.00 mmol) is added slowly by syringe pump over a period of 30 minutes. Finally, a final period of stirring of 30 minutes at 5° C. allows complete conversion of the epoxide. Then, 0.75 mmol of 1,4-dibromobenzene is added to the reaction mixture, to serve as an internal standard for quantification of the reaction products. $^1$H NMR quantitative analysis of the crude reaction product diluted in 2 mL of deuterated dichloromethane ($CD_2Cl_2$) shows that the 7-oxabicyclo[4.1.0]heptane is converted into a mixture made up of 2-hydroperoxycyclohexan-1-ol (HPA) and cyclohexane-1,2-diol, obtained with yields of 34 mol % and 32 mol %, respectively. A TON of 2900 is thus achieved.

Example 8: Perhydrolysis of an Epoxidized Olive Oil

A 6-mL test tube (ø12.25×75×0.80 mm) equipped with a magnetic bar is charged with 332.4 mg of an epoxidized olive oil containing 3.21 mmol/g of epoxide functions. This composition was determined by quantifying the alkene functional groups by quantitative $^1$H NMR of the crude olive oil and by ensuring that the conversion of the alkene functions to epoxides was total. Then 0.13 µmol of hydrated phosphotungstic acid and an aqueous solution of hydrogen peroxide at 60% (w/v) (1.06 mmol) are added. The mixture is stirred at 1000 rev/min at 50° C. for 4 hours. At the end of stirring and at room temperature, 1.5 mL of deuterated methanol and 0.5 mL of deuterated chloroform are added to the crude reaction product and then $^1$H NMR quantitative analysis makes it possible to observe that the epoxidized olive oil has transformed completely into a mixture made up of hydroperoxy alcohols and vicinal diols, obtained with a yield of 73 mol % (as hydroperoxy alcohol functions) and 12 mol % (of vicinal diol functions), respectively. A TON of 5600 is thus achieved.

(1) Li, Y.; Hao, H.-D.; Wu, Y. Facile Ring-Opening of Oxiranes by $H_2O_2$ Catalyzed by Phosphomolybdic Acid. Org. Lett. 2009, 11, 2691-2694. https://doi.org/10.1021/ol900811m.

(2) Payne, G. B.; Smith, C. W. Reactions of Hydrogen Peroxide. III. Tungstic Acid Catalyzed Hydroxylation of Cyclohexene in Nonaqueous Media. J. Org. Chem. 1957, 22, 1682-1685. https://doi.org/10.1021/jo01363a042.

(3) Shinichiro, I.; Sunao, N.; Takuji, N.; Hiroko, K. Hydroperoxyhydroxyoctadecanodecanoate Composition and Method for Producing 9-Oxononanoic Acid Derivative from the Same Composition. JP2003342255 (A), 2003.

(4) Maffucci, A. M.; Perrotti, E.; Santambrogio, A. Epoxidation Reaction with Anhydrous Hydrogen Peroxide. J. Chem. Soc. D 1970, 1198-1199. https://doi.org/10.1039/C29700001198.

(5) Tang, Y.; Dong, Y.; Wang, X.; Sriraghavan, K.; Wood, J. K.; Vennerstrom, J. L. Dispiro-1,2,4-Trioxane Analogues of a Prototype Dispiro-1,2,4-Trioxolane: Mechanistic Comparators for Artemisinin in the Context of Reaction Pathways with Iron(II). J. Org. Chem. 2005, 70, 5103-5110. https://doi.org/10.1021/jo050385+.

(6) Subramanyam, V.; Brizuela, C. L.; Soloway, A. H. Synthesis and Reactions of (3-Hydroxyhydroperoxides. J. Chem. Soc. Chem. Commun. 1976, 508-509. https://doi.org/10.1039/C39760000508.

(7) Ogata, Y.; Sawaki, Y.; Shimizu, H. Rates and Scope of the Oxidative Carbon-Carbon Cleavage of Epoxides by Alkaline Hydrogen Peroxide. J. Org. Chem. 1978, 43, 1760-1763. https://doi.org/10.1021/jo00403a029.

(8) Antonelli, E.; D'Aloisio, R.; Gambaro, M.; Fiorani, T.; Venturello, C. Efficient Oxidative Cleavage of Olefins to Carboxylic Acids with Hydrogen Peroxide Catalyzed by Methyltrioctylammonium Tetrakis(Oxodiperoxotungsto) Phosphate(3-) under Two-Phase Conditions. Synthetic Aspects and Investigation of the Reaction Course. J. Org. Chem. 1998, 63, 7190-7206. https://doi.org/10.1021/jo980481t.

(9) Liu, Y.-H.; Zhang, Z.-H.; Li, T.-S. Efficient Conversion of Epoxides into β-Hydroperoxy Alcohols Catalyzed by Antimony Trichloride/SiO2. Synthesis 2008, 3314-3318. https://doi.org/10.10551s-0028-1083147.

(10) Adam, W.; Rios, A. Perhydrolysis of Epoxides. J. Chem. Soc. D 1971, 822b-823. https://doi.org/10.1039/C2971000822B.

(11) Denier, E.; Duguet, N.; Lemaire, M. Thiazolylidene-Catalyzed Cleavage of Methyl Oleate-Derived α-Hydroxy Ketone to the Corresponding Free Aldehydes. ChemSusChem 2015, 8, 2481-2486. https://doi.org/10.1002/cssc.201500462.

The invention claimed is:

1. A process for synthesizing hydroperoxy alcohols of formula (Ia) and/or (Ib):

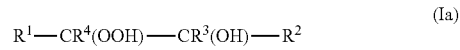

where:
$R^1$ and $R^2$ represent, each independently, an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NR', and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one hydroperoxy and/or hydroxy group, or else $R^1$ and $R^2$ together form a carbocycle consisting of 6 to 12 ring members and optionally substituted, $R^3$ and $R^4$ represent, each independently, a hydrogen atom or an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NR', and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one hydroperoxy and/or hydroxy group, characterized in that it comprises a step of perhydrolysis of the epoxide of formula (II):

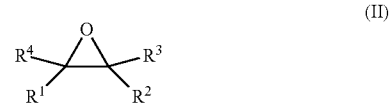

where:
$R^1$ and $R^2$ represent, each independently, an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NR', and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one epoxy group, or else $R^1$ and $R^2$ together form a carbocycle consisting of 6 to 12 ring members and optionally substituted, $R^3$ and $R^4$ represent, each independently, a hydrogen atom or an optionally substituted alkyl group containing from 1 to 20 carbon atoms or a group -L-A where L is a bond or a linear or branched alkylene chain, containing from 1 to 12 carbon atoms, optionally substituted, and A represents a hydrogen atom or a group —COXR in which X denotes an oxygen atom or a group —NR', and R and R' denote, each independently, a group selected from: a hydrogen atom, a $C_1$-$C_6$ alkyl group or a group —($CH_2$)—CH(OCOR$^5$)—CHOCOR$^6$, $R^5$ and $R^6$ denoting, each independently, a linear or branched $C_8$-$C_{22}$ alkyl group optionally substituted and/or interrupted by at least one epoxy group, by reaction with an aqueous solution of hydrogen peroxide, in the presence of a catalyst consisting of phosphotungstic acid, said catalyst representing from 10 to 2000 ppm molar, relative to the number of moles of epoxide of formula (II), and wherein the perhydrolysis reaction is carried out in the absence of a polar protic solvent, said polar protic solvent being an alcohol.

2. The process as claimed in claim 1, characterized in that the catalyst is used in an amount of at least 0.01 wt %, relative to the weight of epoxide.

3. The process as claimed in claim 1, characterized in that the catalyst is used in an amount of at least 50 ppm molar and at most 2000 ppm molar, relative to the molar amount of epoxide.

4. The process as claimed in claim 1, characterized in that the hydrogen peroxide is used in an amount from 1 to 1.5 molar equivalent, relative to the epoxide.

5. The process as claimed in claim 1, characterized in that the perhydrolysis reaction is carried out at a temperature from 5 to 60° C., for a time from 10 minutes to 4 hours.

6. The process as claimed in claim 1, characterized in that the epoxide of formula (II) is the product of epoxidation of a mono- or polyunsaturated fatty acid or of an ester thereof, an alkyl ester or a glyceride of said fatty acid.

7. The process as claimed in claim 6, characterized in that the fatty acid is selected from palmitoleic acid, oleic acid, erucic acid and nervonic acid.

8. The process as claimed in claim 6, characterized in that the fatty acid or its glyceride is derived from a vegetable oil.

9. The process as claimed in claim 6, characterized in that the fatty acid alkyl ester is obtained by transesterification of at least one vegetable oil.

10. The process as claimed in claim 2, characterized in that the catalyst is used in an amount of at least 0.1 wt %, relative to the weight of epoxide.

11. The process as claimed in claim 1, characterized in that hydrogen peroxide is used at a concentration of 30 to 70% (w/v).

* * * * *

UNITED STATES PATENT AND TRADEMARK OFFICE
CERTIFICATE OF CORRECTION

PATENT NO. : 11,512,050 B2
APPLICATION NO. : 17/432504
DATED : November 29, 2022
INVENTOR(S) : Corentin Bordier et al.

It is certified that error appears in the above-identified patent and that said Letters Patent is hereby corrected as shown below:

In the Specification

Column 2,
Line 55, "group —NW," should read --group -NR',--.
Line 61, "else W and" should read --else $R^1$ and--.

Column 3,
Line 2, "group —NW," should read --group -NR',--.
Line 26, "group —NW," should read --group -NR',--.
Line 41, "group —NW," should read --group -NR',--.

Column 8,
Line 48, "<blank>" should read --TABLE 3--.

Column 11,
Line 53, "(3-Hydroxyhydroperoxides." should read --(β-Hydroxyhydroperoxides.--.

Signed and Sealed this
Fifth Day of September, 2023

*Katherine Kelly Vidal*
*Director of the United States Patent and Trademark Office*